United States Patent
Hieber et al.

(10) Patent No.: US 6,313,322 B1
(45) Date of Patent: Nov. 6, 2001

(54) METHOD FOR PRODUCING 3-METHYL 2-BUTENAL ACETALS

(75) Inventors: Gisela Hieber, Heidelberg; Klaus Ebel, Lampertheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/463,847

(22) PCT Filed: Jul. 20, 1998

(86) PCT No.: PCT/EP98/04479

§ 371 Date: Feb. 1, 2000

§ 102(e) Date: Feb. 1, 2000

(87) PCT Pub. No.: WO99/06344

PCT Pub. Date: Feb. 11, 1999

(30) Foreign Application Priority Data

Aug. 1, 1997 (DE) .............................................. 197 33 258

(51) Int. Cl.[7] ...................... C07C 43/303; C07D 317/14; C07D 319/06; C07D 321/06
(52) U.S. Cl. .......................... 549/347; 549/376; 549/430; 568/596
(58) Field of Search .................................. 549/347, 376, 549/430; 568/596

(56) References Cited

FOREIGN PATENT DOCUMENTS

| 629 619 | 12/1994 | (EP) . |
| 1 465 512 | 2/1977 | (GB) . |

OTHER PUBLICATIONS

Organikum, VEB Deutscher Verlag Der Wissenschaften, Berlin 1981, 2berichtigter Nachdruck der 15. Auflage Mit 123.

J.Org.Chem. 1995, 60, 3397–3400, North et al.

Liebigs Ann. Chem. 1986, Hoepfner et al., 99–113.

J.Chem Soc. (C) 1971, 811–816, Bandaranayske et al.

Bull.Soc.Fr. 1965, 1007–1014, Julia et al.

*Primary Examiner*—T. A. Solola
(74) *Attorney, Agent, or Firm*—Keil & Weinkauf

(57) ABSTRACT

A process for preparing acetals of the formula I

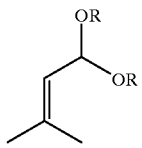

(I)

where a) the Rs are, independently of one another, a $C_1$–$C_{20}$-alkyl or $C_3$–$C_{20}$-alkenyl radical, or b) the two R radicals together form the members of an unsubstituted or $C_1$–$C_{10}$-alkyl-substituted 5- to 7-membered cyclic acetal, by reacting 3-methyl-2-butenal in the presence of sulfamic acid, of a N-($C_1$–$C_8$-alkyl)sulfamic acid or of a N,N-di($C_1$–$C_8$-alkyl)sulfamic acid as catalyst with:

an alcohol of the formula R—OH (IIa), or an orthoester of the formula HC—(OR)$_3$ (III) or a mixture of an alcohol of the formula (IIa) and an orthoester of the formula (III), or an alcohol of the formula HO—(CH$_2$)$_m$—OH (IIb), where m is a number from 2 to 4, and (CH$_2$)$_m$ group in the alcohol IIb may be substituted by a $C_1$–$C_{10}$-alkyl group.

8 Claims, No Drawings

METHOD FOR PRODUCING 3-METHYL 2-BUTENAL ACETALS

This application is a 371 of PCT/EP98/04479 filed Jul. 20, 1998.

The present invention relates to a process for preparing acetals of the formula I

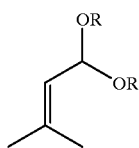

where
a) the Rs are, independently of one another, a $C_1$–$C_{20}$-alkyl or $C_3$–$C_{20}$-alkenyl radical or
b) the two R radicals together form the members of an unsubstituted or $C_1$–$C_{10}$-alkyl-substituted 5- to 7-membered cyclic acetal, reacting 3-methyl-2-butenal in the presence of sulfamic acid, of a N-($C_1$–$C_8$-alkyl)sulfamic acid or of a N,N-di ($C_1$–$C_8$-alkyl)sulfamic acid as catalyst with in case (a)
a1) an alcohol of the formula IIa

  R—OH  (IIa)

where R has the meaning stated under (a),
a2) an orthoester of the formula (III)

  HC—(OR)$_3$  (III)

where R has the meaning stated under (a) or
a3) a mixture of an alcohol of the formula (IIa) and an orthoester of the formula (III),
and in case (b)
b) with an alcohol of the formula IIb

  HO—(CH$_2$)$_m$—OH  (IIb)

where m is a number from 2 to 4, and a methylene group in the alcohol IIb may be substituted by a $C_1$–$C_{10}$-alkyl group.

The N-($C_1$–$C_8$-alkyl)sulfamic acids and N,N-di($C_1$–$C_8$-alkyl)sulfamic acids are called "alkylsulfamic acids" for short in the following text.

Known processes for preparing acetals of 3-methyl-2-butenal from 3-methyl-2-butenal and the corresponding alcohols use a variety of acidic catalysts. The following acids are normally employed as catalysts: phosphoric acid, ammonium nitrate, p-toluenesulfonic acid and potassium bisulfate.

Bull. Soc. Fr. 1965, 1007–1014 discloses the use of phosphoric acid. 3-Methyl-2-butenal is stirred with ethanol, triethyl orthoformate and phosphoric acid at room temperature for 40 hours. The reaction mixture is then taken up in ether, washed with 0.5 N aqueous ammonia and dried over sodium sulfate. Subsequent distillation affords 3-methyl-2-butenal diethyl acetal in a yield of 65%.

Liebigs Ann. Chem. 1986, 99–113 describes the reaction of 3-methyl-2-butenal with trimethyl or triethyl orthoformate and the corresponding alcohol using ammonium nitrate as catalyst. After reaction at room temperature for 8 hours, the undissolved catalyst is filtered off and, after addition of potassium carbonate, the reaction mixture is distilled. The dimethyl acetal is isolated in a yield of 63%, and the diethyl acetal is isolated in a yield of 51%.

The use of p-toluenesulfonic acid is described in J. Chem. Soc. (C) 1971, 811–816: 3-methyl-2-butenal, methanol and trimethyl orthoformate are stirred with p-toluenesulfonic acid at room temperature for 24 hours. The reaction mixture is then diluted with water and extracted with ether. The organic phase is washed with water and aqueous sodium bicarbonate solution, dried and distilled. The distillate still contains 10% 3-methyl-2-butenal. Nothing is stated about the yield.

Various acidic catalysts were tested in J. Org. Chem. 1995, 60, 1995, 3397–3400. Use of p-toluenesulfonic acid resulted in polymerization of the 3-methyl-2-butenal. Triethylammonium chloride, pyridinium p-toluenesulfonate, tetrabutylammonium bisulfate and ammonium bisulfate likewise gave unsatisfactory results. Potassium bisulfate proved to be more suitable. The reaction conditions are likewise described in the Patent Application EP 0629619. Triethyl orthoformate and 3-methyl-2-butenal are added to abs. ethanol at 4° C. The clear solution is cooled to 2° C., and potassium bisulfate is added. The heterogeneous reaction mixture warms to 10° C. owing to the exothermic reaction. The mixture is then allowed to warm to 21° C. over the course of 45 minutes and is then stirred at this temperature for 15 minutes. The catalyst is then filtered off and washed with ethanol. The filtrate is mixed with potassium carbonate and stirred at room temperature for one hour. The potassium carbonate is then likewise filtered off and washed with ethanol. Distillation affords 3-methyl-2-butenal dimethyl acetal in a yield of 85%. The disadvantages of this process are that elaborate temperature control is required and the alternating cooling and warming steps require increased energy consumption and elaborate apparatus.

Even cyclic acetals, which ought to be obtained in far better yields because of their greater stability, are, according to DE U.S. Pat. No. 2,334,378, isolated only in yields comparable to those of the open-chain representatives (63–88%). According to this, 3-methyl-2-butenal and various 1,3-diols are heated with dichloromethane using a water trap. The catalyst used is p-toluenesulfonic acid. Excess 1,3-diol and p-toluenesulfonic acid are removed with water after the reaction is complete. The organic phase is fractionally distilled.

The disadvantages of previously disclosed processes using said acid are either moderate yields, long reaction times or elaborate workup methods, frequently as a consequence of the poor solubility of the acidic catalyst. It is common to all the processes that the acidic catalyst is removed from the reaction mixture either by a filtration step or by a wash with water and/or aqueous alkaline solutions.

It is an object of the present invention to provide a process which does not have the disadvantages of the prior art and, in particular, makes it possible to synthesize acetals of 3-methyl-2-butenal in high yields in an industrially straightforward manner.

We have found that this object is achieved by the process defined at the outset.

The novel process is, in the case of the preparation of compounds of type (a) of formula (I), particularly suitable for those formed from $C_1$–$C_{20}$-alkyl alcohols such as methanol, ethanol, propanol, isopropanol, butanol, sec-butanol and t-butanol, and $C_3$–$C_{20}$-alkenyl alcohols such as propenol, butenol, pentenol and 3-methyl-2-butenol, from the corresponding orthoesters of the formula (III) whose 3 alkoxy radicals are derived from the aforementioned alcohols, and/or from mixtures of the aforementioned alcohols and orthoesters.

If the alcohols of the formula (IIa) and the orthoesters of the formula (III) are used in the form of a mixture, the molar ratio thereof can vary within a wide range and is generally from 0.01:1 to 20:1, preferably 0.1:1 to 5:1.

In the case of the preparation of compounds of the formula (I) of type (b), suitable alcohols of the formula (IIb) are those which form with the carbonyl group of 3-methyl-2-butenal an unsubstituted or $C_1$–$C_{10}$-alkyl-substituted acetal, in particular $C_1$–$C_{10}$-alkyl-substituted $C_2$–$C_4$-diols such as 1,2-ethanediol, 1,2-propanediol, 1,3-propanediol, 1,2-butanediol, 1,3-butanediol, 2,4-pentanediol, 2-methyl-2,4-butanediol and 2,2-dimethyl-1,3-propanediol.

Sulfamic acid or alkylsulfamic acid is employed according to the invention as catalyst in this process in a concentration of from 0.001 to 10, preferably from 0.001 to 5, mol% based on 3-methyl-2-butenal.

In the novel process for preparing acetals of the formula (I) of type (a), 3-methyl-2-butenal, alcohols of the formula (IIa) or orthoesters of the formula (III) are employed preferably in a molar ratio (R1), formed from the amount of 3-methyl-2-butenal and the amount of units which are derived from these alcohols and orthoesters and are of the formula (IVa)

—OR        (IVa)

where R has the same meaning as in formula (I), which is from 0.5:1 to 0.01:1, particularly preferably 0.4 to 0.05, taking only 2/3 of the amount of units of the formula (IVa) derived from orthoesters of the formula (III) into account.

To prepare acetals of type (b), 3-methyl-2-butenal and alcohols of the formula IIb are generally employed in a molar ratio (R2) of from 0.02:1 to 1:1.

The product of the formula (I) is generally required to be homogeneous, with the radical R always being the same hydrocarbon group, and correspondingly the alcohols of the formula (IIa) and the orthoesters of the formula (III), or the alcohols of the formula (IIb), are then chosen so that the radical R in the starting materials is also the same alkyl, alkenyl or alkanediyl group.

Since the acetalization of aldehydes with alcohols is an equilibrium reaction in which, in most cases, the equilibrium is not entirely on the acetal side, it is in many cases necessary, in order to optimize the yield, for the water formed in the reaction of 3-methyl-2-butenal with the alcohols of the formula (IIa) or (IIb) to be removed continuously from the reaction mixture.

There are in principle 2 different possibilities for removing the water of reaction from the mixture.

In the first method, the reaction is carried out in the presence of an inert organic solvent which forms an azeotrope with water and is so poorly miscible with water at room temperature that the only mixtures predominantly containing the organic solvent which exist are those which contain less water at room temperature than does the azeotrope, and the water is distilled out with the latter. The azeotrope is then normally condensed, preferably cooled to a temperature below room temperature, the aqueous phase which is formed is separated off, and the organic phase is returned to the reaction mixture. This method, generally known as azeotropic distillation, and the solvents suitable for this purpose (water entrainers) are described, for example, in Organikum, VEB Deutscher Verlag der Wissenschaften, Berlin 1981, 2nd, corrected, impression of the 15th Edition, Chapter 2.3.5.

Also suitable as water entrainers are, if acetalization with these alcohols is intended, alcohols having 5 to 20 carbon atoms, which are used in a concentration of from 50 to 99% of the weight of the reaction mixture.

Orthoesters of the formula (III) are generally not employed if the water is removed by the azeotropic distillation process.

In the preparation of acetals of type (a) of the formula (I), the water formed in the reaction can, by another method, be chemically bound by employing a mixture of orthoester of the formula (III) and alcohols of the formula (IIa). The orthoester reacts with the water to give the monoester and thereby liberates 2 equivalents of the alcohol, which is then also available as starting material for the acetalization. The orthoester is therefore advantageously employed in amounts such that it is able to bind both the water derived from the reaction of 3-methyl-2-butenal with the originally employed alcohol, and the water derived from the reaction of 3-methyl-2-butenal with the alcohol formed from the orthoester during the reaction.

For this reason, at least 0.5, preferably 0.5 to 2, mol of orthoester are normally employed per mole of alcohol able to react with 3-methyl-2-butenal, with the proviso that the amount of alcohol exceeding twice the amount of 3-methyl-2-butenal originally present, and unable to react with the aldehyde according to the laws of stoichiometry, is left out of account in this.

The temperature in this type of reaction does not require accurate control and can be, in general, in the range from −20 to 150° C.

The pressure to be applied during the reaction is likewise not critical and is normally from 0.1 to 1.5 bar.

The reaction is complete in practice when the bulk of the 3-methyl-2-butenal has been consumed. This is generally the case after a reaction time of from 20 min to 20 h.

Since sulfamic acid and alkylsulfamic acids are soluble in the reaction mixture, the latter can be worked up particularly simply by adding an amount of a base, preferably of an alkali metal or alkaline earth metal carbonate, eg. potassium carbonate, or of an amine, which is sufficient to neutralize the sulfamic acid, and subsequently distilling directly.

EXPERIMENTAL PART

EXAMPLE 1

76 g (2.37 mol) of methanol, 220 g (2.07 mol) of trimethyl orthoformate and 330 mg (3.4 mmol) of sulfamic acid were mixed and, over a period of 2.5 hours, 125 g (1.49 mol) of 3-methyl-2-butenal were added dropwise. The temperature rose to 33° C. as a result of the exothermic reaction. After stirring for a further 1.5 hours, the mixture was weighed (412.3 g), and 1 g of $K_2CO_3$ was added. The content of 3-methyl-2-butenal dimethyl acetal determined by GC analysis was 43.7% by weight. The yield calculated from this was 93%.

EXAMPLE 2

38 g (1.18 mol) of methanol, 171.7 g (1.62 mol) of trimethyl orthoformate and 30 mg (0.31 mmol) of sulfamic acid were mixed and, over the course of one hour, 125 g (1.49 mol) of 3-methyl-2-butenal were added dropwise. The temperature rose to 34° C. as a result of the exothermic reaction. The reaction mixture was stirred for a further 3 hours and then weighed (330.4 g), and 1 g of $K_2CO_3$ was added. The content of 3-methyl-2-butenal dimethyl acetal determined by GC analysis was 53.3% by weight. The yield calculated from this was 91%.

EXAMPLE 3

268.5 g (8.39 mol) of methanol, 1313.2 g (12.39 mol) of trimethyl orthoformate and 210 mg (2.17 mmol) of sulfamic acid were mixed and, over the course of one hour, 875 g (10.42 mol) of 3-methyl-2-butenal were added dropwise. The temperature rose to 45° C. as a result of the exothermic reaction. The reaction mixture was stirred for a further 4 hours and then weighed (2401.7 g), and 17 g of $K_2CO_3$ were added. The content of 3-methyl-2-butenal dimethyl acetal measured by GC analysis was 51.7% by weight. The yield calculated from this was 91.7%. Distillation of the reaction mixture afforded 1116.5 g of 3-methyl-2-butenal dimethyl acetal in a purity of 98.8% (8.49 mol). The yield was 81.5%.

EXAMPLE 4

106.6 g (2.32 mol) of ethanol, 306 g (2.07 mol) of triethyl orthoformate and 330 mg (3.4 mmol) of sulfamic acid were mixed and, over the course of 2.5 hours, 125 g (1.49 mol) of 3-methyl-2-butenal were added dropwise while cooling in ice. The reaction mixture was stirred for a further 1.5 hours and then weighed (535.7 g), and 10 g of $K_2CO_3$ were added. The content of 3-methyl-2-butenal diethyl acetal determined by GC analysis was 42.7% by weight. The yield calculated from this was 97%. Distillation of the reaction mixture afforded 174.6 g of 3-methyl-2-butenal diethyl acetal in a purity of 98.6% (1.09 mol; 73.1% yield). Taking into account a mixed fraction of 145.5 g which contained 21.8% of the acetal (0.2 mol), the overall isolated yield was 86.6%.

General Preparation Method for Examples 5 to 8 and Comparative Examples 1 to 8

The catalyst indicated in Table 1 or 2 was dissolved, if possible, in 1.6 equivalents of methanol. The resulting solution was added dropwise to a mixture of one equivalent of 3-methyl-2-butenal and 1.4 equivalents of trimethyl orthoformate. The temperature was kept below 30° C. by cooling in ice in the case of exothermic reactions. If the reaction rate was too slow, the mixture was refluxed. In cases where the catalyst was not soluble in methanol, 3-methyl-2-butenal and trimethyl orthoformate were added dropwise to a mixture of catalyst and methanol.

The other reaction conditions and the yields can be found in Tables 1 and 2.

TABLE 1

Examples

| Examples | Catalyst | Mol % Catalyst | Temperature [° C.] | Reaction time [h] | GC Analysis [in % area] 3-Methyl-2-butenal | GC Analysis [in % area] 3-Methyl-2-butenal dimethyl acetal |
|---|---|---|---|---|---|---|
| 5 | $H_2NSO_3H$ | 4.6 | 32 | 1 | 0 | 50.76 |
| 6 | $H_2NSO_3H$ | 2.3 | 10–12 | 2.5 | 0 | 51.29 |
| 7 | $H_2NSO_3H$ | 0.23 | 31 | 3.5 | 0 | 60.31 |
| 8 | $H_2NSO_3H$ | 0.23 | 33 | 3.5 | 0 | 61.62 |

TABLE 2

Comparative Examples

| Comp. Ex. | Catalyst | Mol % Catalyst | Temperature [° C.] | Reaction time [h] | GC-Analysis [in % area] 3-Methyl-2-butenal | GC-Analysis [in % area] 3-Methyl-2-butenal dimethyl acetal |
|---|---|---|---|---|---|---|
| 1 | $H_2SO_4$ | 2.4 | 24–28 | 1 | 0.71 | 0.84 |
| 2 | $(NH_4)_2SO_4$ | 4.6 | 24–50 | 27 | 3.93 | 57.74 |
| 3 | $(NH_4)_2SO_4$ | 4.6 | 54 | 68 | 3.01 | 57.91 |
| 4 | HOAc | 4.6 | 50 | 24 | 34.95 | 16.50 |
| 5 | $NH_4HSO_4$ | 4.6 | 30 | 3 | 0.14 | 13.74 |
| 6 | HCOOH | 4.6 | 50 | 44 | 3.35 | 57.48 |
| 7 | $NH_4Cl$ | 4.6 | 40 | 24 | 0.31 | 61.77 |
| 8 | $NH_4HCO_2$ | 4.6 | 40 | 18 | 33.6 | 2.28 |

We claim:

1. A process for preparing acetals of the formula I

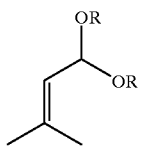

(I)

where a) the Rs are, independently of one another, a $C_1$–$C_{20}$-alkenyl radical, or b) the two Rs together form —$(CH_2)_m$—, where m is a number from 2 to 4, and —$(CH_2)_m$— is optionally substituted by a $C_1$–$C_8$-alkyl group, comprising:

reacting 3-methyl-2-butenal in the presence of a catalyst selected from the group consisting of sulfamic acid, a N-($C_1$–$C_8$-alkyl)sulfamic acid and a N,N-di ($C_1C_8$-alkyl)sulfamic acid with an alcohol of the formula IIa R—OH  (IIa), or
an orthoester of the formula (III)

$$HC-(OR)_3 \quad (III),$$

or
a mixture thereof, or
with an alcohol of the formula IIb $$HO-(CH_2)_m-OH \quad (IIb).$$

2. A process as claimed in claim 1, wherein sulfamic acid, a N-($CH_1$–$C_8$-alkyl)sulfamic acid or a N-N-di($C_1$–$C_8$-alkyl) sulfamic acid is used in a concentration of from 0.001 to 10 mol % based on 3-methyl-2-butenal.

3. A process as claimed in claim 1, wherein the water formed in the reaction of 3-methyl-2-butenal with the alcohols of the formula (IIa) or (IIb) is removed continuously from the reaction mixture.

4. A process as claimed in claim 1, wherein the alcohols of the formula (IIa) and the orthoesters of the formula (III) are used in a molar ratio of form 0.1:1 to 20:1.

5. A process as claimed in claim 1, wherein 3-methyl-2-butenal, and the alcohols of the formula (IIa) are in a molar ratio ($R_1$) of from 0.5:1 to 0.01:1.

6. A process as claimed in claim 1, wherein 3-methyl-2-butenal and the alcohols of the formula (IIb) are used in a molar ratio ($R_2$) of from 0.2:1 to 1:1.

7. A process as claimed in claim 1, wherein R in the alcohols of the formula (IIa) or (IIb), or the orthoesters of the formula (III), or in a mixture of alcohol (IIa) and orthoester (III), is the same.

8. A process as claimed in claim 7, wherein R is $C_5$–$C_{20}$-alkyl or $C_5$–$C_{20}$-alkenyl, and the alcohol is in a concentration of 50–99% of the weight of the reaction mixture.

* * * * *

UNITED STATES PATENT AND TRADEMARK OFFICE
CERTIFICATE OF CORRECTION

PATENT NO. : 6,313,322 B1 Page 1 of 1
DATED : November 6, 2001
INVENTOR(S) : Hieber et al.

It is certified that error appears in the above-identified patent and that said Letters Patent is hereby corrected as shown below:

Column 6,
Line 56, after "another," insert -- a $C_1$-$C_{20}$-alkyl or --.

Column 7,
Line 13, "N-($CH_1$-$C_8$-alkyl)" should be -- N-($C_1$-$C_8$-alkyl) --.

Signed and Sealed this

Eleventh Day of November, 2003

JAMES E. ROGAN
*Director of the United States Patent and Trademark Office*